US012080402B2

United States Patent
Hakala et al.

(10) Patent No.: US 12,080,402 B2
(45) Date of Patent: Sep. 3, 2024

(54) ARTIFICIAL INTELLIGENCE MODELING TO SUGGEST FIELD GEOMETRY TEMPLATES

(71) Applicant: SIEMENS HEALTHINEERS INTERNATIONAL AG, Steinhausen (CH)

(72) Inventors: Mikko Hakala, Rajamäki (FI); Esa Kuusela, Espoo (FI); Elena Czeizler, Helsinki (FI); Shahab Basiri, Siuntio (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 406 days.

(21) Appl. No.: 17/361,085

(22) Filed: Jun. 28, 2021

(65) Prior Publication Data

US 2022/0415472 A1 Dec. 29, 2022

(51) Int. Cl.
| | |
|---|---|
| G16H 20/40 | (2018.01) |
| A61N 5/10 | (2006.01) |
| G06F 18/21 | (2023.01) |
| G06N 20/00 | (2019.01) |
| G16H 10/60 | (2018.01) |

(52) U.S. Cl.
CPC ........... *G16H 20/40* (2018.01); *A61N 5/1047* (2013.01); *G06F 18/217* (2023.01); *G06N 20/00* (2019.01); *G16H 10/60* (2018.01)

(58) Field of Classification Search
CPC ........ G16H 50/70; G16H 30/40; G16H 50/20; G16H 50/00; G16H 20/40
See application file for complete search history.

(56) References Cited

U.S. PATENT DOCUMENTS

2020/0353286 A1* 11/2020 Wu .................. A61N 5/1031
2021/0027878 A1 1/2021 He et al.
2022/0093242 A1 3/2022 Hakala et al.

FOREIGN PATENT DOCUMENTS

WO WO-2019179857 A1 * 9/2019 ........... A61N 5/1038

OTHER PUBLICATIONS

Moreau, Grégoire, et al. "Reinforcement learning for radiotherapy dose fractioning automation." Biomedicines 9.2 (2021): 214. (Year: 2021).*

(Continued)

*Primary Examiner* — Jason B Dunham
*Assistant Examiner* — Constantine Siozopoulos
(74) *Attorney, Agent, or Firm* — FOLEY & LARDNER LLP

(57) ABSTRACT

Embodiments described herein provide for recommending radiotherapy treatment attributes. A machine learning model predicts the preference of a medical professional and provides relevant suggestions (or recommendations) of radiotherapy treatment attributes for various categories of radiotherapy treatment. Specifically, the machine learning model predicts field geometry attributes from various field geometry attribute options for various field geometry attribute categories. The machine learning model is conditioned on patient data such as medical images and patient information. The machine learning model is trained in response to cumulative reward information associated with a medical professional accepting the provided/displayed recommendations.

20 Claims, 8 Drawing Sheets

(56) References Cited

OTHER PUBLICATIONS

Surmenok, Pavel, "Contextual Bandits and Reinforcement Learning," Towards Data Science: A Medium Publication Sharing Concepts, Ideas and Codes, 8 pages, retrieved Jun. 28, 2021, from https://towardsdatascience.com/contextual-bandits-and-reinforcement-learning-6bdfeaece72a.
Vowpal Wabbit website, https://vowpalwabbit.org/.
ISR and Written Opinion on PCT Application PCT/EP2022/067537, Oct. 17, 2022 (13 pages).

* cited by examiner

| Categories | Radiotherapy Treatment Attributes | | |
|---|---|---|---|
| Radiation Therapy Treatment Technique 301 | VMAT 302 <ul><li>Standard (two full arcs)</li><li>Complex (two partial arcs)</li><li>Complex (three arcs)</li><li>Complex (four arcs)</li></ul> | IMRT 303 | |
| Couch Rotation 310 | <ul><li>Rotate Couch</li><li>Do not Rotate Couch</li><li>Rotate Couch x degrees</li></ul> 312 | | |
| Collimator Angle Settings 320 | <ul><li>Default values</li><li>Non-default values</li><li>Arc start angle</li><li>Arc stop angle</li></ul> 322 | | |

FIG. 3

ARTIFICIAL INTELLIGENCE MODELING TO SUGGEST FIELD GEOMETRY TEMPLATES

TECHNICAL FIELD

This application relates generally to using artificial intelligence modeling to suggest radiotherapy treatment attributes in radiation therapy treatment procedures.

BACKGROUND

Radiotherapy (radiation-based therapy) is used as a cancer treatment by emitting high doses of radiation that can kill cells or shrink a tumor. Due to the extreme nature of the radiation emitted from the radiation therapy machine, it is imperative that treatment attributes are precisely calculated and followed. The target region of a patient's anatomy that is intended to receive radiation (e.g., tumor) is referred to as the planning target volume (PTV). The goal is to deliver enough radiation to the PTV to kill the cancerous cells during the radiotherapy treatment. However, other organs or anatomical regions that are adjacent to, or surrounding, the PTV can be in the way of radiation beams and can receive enough radiation to damage or harm such organs or anatomical regions. These organs or anatomical regions are referred to as organs at risk (OARs).

Field geometry refers to various attributes of a radiotherapy machine configured for the patient's treatment. Field geometry attributes include intensity-modulated radiation therapy (IMRT) parameters (e.g., the number of radiation beams and the beam angles (radiation delivery directions)), volumetric modulated arc therapy (VMAT) parameters (e.g., number and extent of arcs (full or partial)), collimator angles, collimator jaw positions, avoidance sectors, isocenter positioning strategy, couch rotation, and the like.

The choices involved with determining effective and appropriate field geometry attributes and other radiotherapy attributes depend on various factors such as the treatment machines available at the clinic, the clinic's guidelines, the medical professional's preferences (where the medical professional is a treatment planner, technician, physician, clinician, dosimetrist, oncologist, clinical experts, or radiologist (or some combination)), patient anatomy, among others.

Various medical professionals may manually select field geometry attributes using their subjective understanding and skill in conjunction with various external and internal guidelines. However, this conventional method is inefficient. For instance, as the first step of the field geometry selection, medical professionals may identify the treatment modality (e.g., choose between VMAT or IMRT). Medical professionals may then decide whether a coplanar or non-coplanar treatment is preferred. Medical professionals may then determine beam limiting device angles for the treatment. In the case of IMRT, the beam delivery directions and number of beams are the specifically relevant variables that must be decided, whereas for VMAT, the medical professional may need to choose the number of arcs and their corresponding start and stop angles.

For these decisions, each clinic and/or medical professional may have a preference and standard practice. For instance, a first medical professional may place the radiation isocenter directly onto the subject area (e.g., tumor) and may decide to have a full arc of gantry motion around the subject area. Another medical professional may approach the same field geometry determination by having a few fixed field directions and attempt to avoid other organs. Further, field geometry determinations may vary across regions and/or clinics. In some cases, clinics may define their own field geometry attributes to homogenize treatment across the patients of the institution. In other cases, as discussed herein, medical professionals may define field geometry attributes based on personal preferences, training, and unique ways of interpreting patient data (e.g., patient medical files, patient medical images). Therefore, patient data may be interpreted in different ways, which has produced undesirable results.

Selecting the various field geometry attributes may be considered a multiclass classification problem in which there may be various classes and more than one class is acceptable and/or considered. Conventionally, field geometry attributes may be selected according to generative adversarial networks (GAN), statistical relational learning with Markov Logic Networks and other solutions based on patient similarity (found via dimensionality reduction, for example). However, the conventional approaches assume the existence of a representative training set prior to training the implemented machine learning models. Further, the conventional approaches are sensitive to data distribution changes.

SUMMARY

For the aforementioned reasons, there is a need to recommend field geometry attributes using methods and systems that do not depend on subjective skills and understanding of medical professionals. Disclosed herein are systems and methods capable of offering continually refined, medical professional-specific recommendations of field geometry attributes for a patient. Using the medical professional's prior decisions and continual interactions, a continuously trained (e.g., online learning) recommendation algorithm is implemented to select field geometry attributes for a patient.

Continuously learning allows a machine learning model to learn without a predefined training set because the learning occurs online. For each new patient, performance of the field geometry recommendation system is maximized. Continuously learning also allows the machine learning model to gradually adopt to new data distributions (e.g., via an exploration phase), making the machine learning model less sensitive (more resistant) to data distribution changes. For example, in some implementations, a new solution(s) (e.g., field geometry attribute, radiotherapy treatment attribute and/or category of radiotherapy treatment) may be added and as time evolves, the machine learning model is able to accommodate the new solution(s).

The machine learning model may be trained using a reinforcement learning approach. The reinforcement learning approach utilizes agents and a dynamically changing (e.g., learning) policy to determine radiotherapy treatment attribute recommendations and specifically field geometry attribute recommendations. The field geometry attributes (e.g., a set of recommended field geometry attributes) recommended by the reinforcement learning approach may be considered a field geometry template.

The reinforcement learning approach learns a refined policy to recommend relevant field geometry attributes for a medical professional depending on the patient data as context. Patient data may include medical images (computed tomography (CT) images, cone beam CT images (CBCT), four-dimensional CT images (e.g., CT images over time), magnetic resonance imaging (MRI) images, positron emission tomography (PET) images, ultrasound images, images obtained via some other imaging modality, or a combination thereof), patient information (e.g., height, weight, body mass index (BMI), diagnosis information (including anatomical attributes such as PTVs and/or OARs), age, equipment (e.g., pacemaker, respirator)), and the like. The reinforcement learning approach uses continual user interactions to make radiotherapy attribute recommendations (and specifically field geometry attribute recommendations) for specific medical professionals and clinics.

A reinforcement learning approach for recommending field geometry class solutions for the medical professionals is described herein. The reinforcement learning approach replicates (or simulates) the way in which a medical professional would determine field geometry attributes. Attributes of field geometry are selected for each patient using continual user interactions. A full reinforcement learning approach may not be applicable because each context (e.g., each reinforcement learning state) does not depend on the past actions of the agent. That is, the reinforcement learning approach described herein may be a lightweight reinforcement learning approach such as contextual bandits. The reinforcement learning approach may be applied as a one-step reinforcement learning approach.

A machine learning model predicts the preference of a medical professional and provides relevant suggestions (or recommendations) of radiotherapy treatment attributes for various categories of radiotherapy treatment. Specifically, the machine learning model uses a reinforcement learning approach to predict field geometry attributes from various field geometry attribute options for various field geometry attribute categories. The machine learning model is conditioned on patient data (e.g., medical images, patient information). The machine learning model is trained in response to cumulative reward information associated with a medical professional accepting the provided/displayed recommendations.

In an embodiment, a computer-implemented method may comprise iteratively training, by a processor, a machine learning model, wherein in at least one iteration, the processor: executes the machine learning model to ingest patient data to select a predicted radiotherapy treatment attribute from a plurality of treatment attribute options for a category of radiotherapy treatment from a plurality of categories of radiotherapy treatment; in response to displaying the plurality of treatment attribute options on an electronic device, receives a selection of at least one attribute; calculates a reward value for the predicted radiotherapy treatment attribute, wherein when the selection matches the predicted radiotherapy treatment attribute, the processor adjusts the reward value upwards; generates a subsequent predicted radiotherapy treatment attribute corresponding to a subsequent category of radiotherapy treatment, the processor selecting the subsequent category of radiotherapy treatment based on the selection of at least one radiotherapy treatment attribute received from the electronic device; and calculates a subsequent reward value for the subsequent predicted radiotherapy treatment attribute, wherein the processor trains a policy to generate a combination of predicted radiotherapy treatment attributes that generates a cumulative reward value that satisfies a threshold.

At least one category within the plurality of categories of radiotherapy treatment may correspond to: radiation therapy treatment techniques, couch rotation, or collimator angle settings.

The processor may display the plurality of treatment attribute options on the electronic device operated by a user, such that the machine learning model may be trained based on the user's preferences.

The patient data may comprise at least one of a patient's anatomical attribute, a body mass index, a medical image, a patient height, a patient weight, a patient age, diagnosis information, or a patient equipment.

The subsequent category may be selected using a workflow for radiotherapy treatment.

Each category of radiotherapy treatment may correspond to a category of a field geometry.

The computer-implemented method may further comprise executing by the processor, the trained machine learning model using data associated with a second patient; and displaying, by the processor, a second predicted radiotherapy treatment attribute that is predicted to produce a higher reward than other treatment attribute options.

The cumulative reward value satisfying the threshold may indicate that the cumulative reward value is higher than other cumulative reward values associated with other possible predicted radiotherapy treatment attributes.

At least one radiotherapy treatment attribute may correspond to: a standard VMAT with two full arcs, a complex VMAT with two partial arcs, a complex VMAT with three arcs, a complex VMAT with four arcs, rotate couch, do not rotate couch, rotate couch a predetermined number of degrees, a default value collimator angle, a non-default value collimator angle, a collimator angle arc start, or a collimator angle arc stop.

The machine learning model may be trained using one-step reinforcement learning.

In another embodiment, a system may comprise a server comprising a processor and a non-transitory computer-readable medium containing instructions that when executed by the processor causes the processor to perform operations comprising: iteratively train a machine learning model, wherein in at least one iteration, the processor: executes the machine learning model to ingest patient data to select a predicted radiotherapy treatment attribute from a plurality of treatment attribute options for a category of radiotherapy treatment from a plurality of categories of radiotherapy treatment; in response to displaying the plurality of treatment attribute options on an electronic device, receives a selection of at least one attribute; calculates a reward value for the predicted radiotherapy treatment attribute, wherein when the selection matches the predicted radiotherapy treatment attribute, the processor adjusts the reward value upwards; generates a subsequent predicted radiotherapy treatment attribute corresponding to a subsequent category of radiotherapy treatment, the processor selecting the subsequent category of radiotherapy treatment based on the selection of at least one radiotherapy treatment attribute received from the electronic device; and calculates a subsequent reward value for the subsequent predicted radiotherapy treatment attribute, wherein the processor trains a policy to generate a combination of predicted radiotherapy treatment attributes that generates a cumulative reward value that satisfies a threshold.

At least one category within the plurality of categories of radiotherapy treatment may correspond to: radiation therapy treatment techniques, couch rotation, or collimator angle settings.

The processor may be further configured to display the plurality of treatment attribute options on the electronic device operated by a user such that the machine learning model is trained based on the user's preferences.

The patient data may comprise at least one of a patient's anatomical attribute, a body mass index, a medical image, a patient height, a patient weight, a patient age, diagnosis information, or a patient equipment.

The subsequent category may be selected using a workflow for radiotherapy treatment.

Each category of radiotherapy treatment may correspond to a category of a field geometry.

The processor may be further configured to: execute the trained machine learning model using data associated with a second patient; and display a second predicted radiotherapy treatment attribute that is predicted to produce a higher reward than other treatment attribute options.

The cumulative reward value satisfying the threshold may indicate that the cumulative reward value is higher than other cumulative reward values associated with other possible predicted radiotherapy treatment attributes.

At least one radiotherapy treatment attribute may correspond to: a standard VMAT with two full arcs, a complex VMAT with two partial arcs, a complex VMAT with three arcs, a complex VMAT with four arcs, rotate couch, do not rotate couch, rotate couch a predetermined number of degrees, a default value collimator angle, a non-default value collimator angle, a collimator angle arc start, or a collimator angle arc stop.

The machine learning model is trained using one-step reinforcement learning.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 3 illustrates categories of radiotherapy treatment and radiotherapy treatment attributes, according to an embodiment.

DETAILED DESCRIPTION

Figure 1:
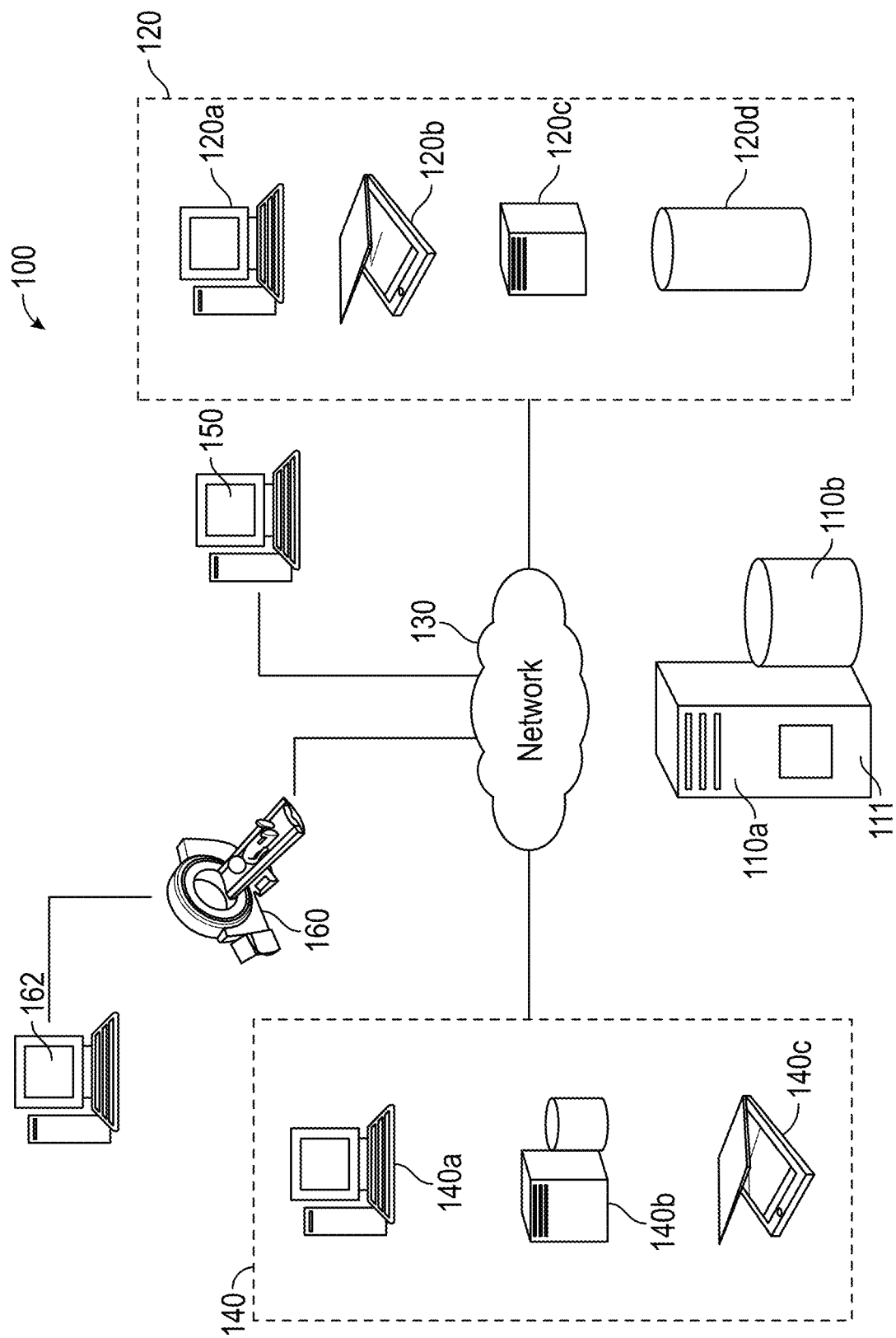
FIG. 1 illustrates components of a radiotherapy treatment attribute recommendation system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Radiotherapy clinics may utilize dynamic software solutions to recommend radiotherapy treatment attributes. Specifically, the software solutions may analyze patient data, medical professional preferences, and a multitude of other factors to generate customized recommended field geometry attributes.

FIG. 1 illustrates components of a radiotherapy treatment attribute recommendation system 100, according to an embodiment. The system 100 may include an analytics server 110a, system database 110b, machine learning models 111, electronic data sources 120a-d (collectively electronic data sources 120), end-user devices 140a-c (collectively end-user devices 140), an administrator computing device 150, and a medical device 160 having a medical device computer 162. Various components depicted in FIG. 1 may belong to a radiotherapy clinic at which patients may receive radiotherapy treatment, in some cases via one or more radiotherapy machines located within the clinic (e.g., medical device 160). The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may generate and display an electronic platform configured to use various computer models 111 (including artificial intelligence and/or machine learning models) to recommend field geometry attributes. More specifically, the platform may display one or more optimized (recommended, identified, selected) radiotherapy treatment attributes such as field geometry attributes determined from the machine learning models 111. The electronic platform may include graphical user interface (GUI) displayed on each electronic data source 120, the end-user devices 140, the administrator computing device 150, and/or the medical device computer 162. An example of the electronic platform generated and hosted by the analytics server 110a may be a web-based application or a website configured to be displayed on different electronic devices, such as mobile devices, tablets, personal computer, and the like.

In a non-limiting example, a medical professional may input predefined sets of classes of field geometries (e.g., IMRT, VMAT, couch rotation) to electronic data source 120b. The predefined sets of field geometry class solutions may be the solution set from which the recommendations will be drawn. The medical professional may interact with the electronic data source 120*b* (and other components of system 100 including medical professional device 140*c* and medical computing device 162) such that the medical professional can interact with outputs of the machine learning models 111 (e.g., provide feedback to the machine learning models 111, select a desired radiotherapy treatment attribute of displayed radiotherapy treatment attribute options). The electronic data source 120*b* (and other components of system 100 including medical professional device 140*c* and medical computing device 162) may also be configured to monitor or otherwise record medical professional inputs such that the input of the medical professional is captured and stored.

A medical professional may input patient data such as medical images, and PTV and/or OAR information to electronic data source 120*b*. The medical professional operating devices 120*b*, 140*c*, and/or 162, may access the platform and review displayed recommended field geometry attributes generated from the machine learning model 111.

Additionally or alternatively, the operations invoked by the analytics server 110*a* to recommend field geometry attributes may be part of the operations in a sequence of operations to optimize a patient treatment plan (e.g., dose distribution among the patient's organs). That is, the results of the machine learning model 111 and the medical professional's selection may be transmitted to other processors or devices to optimize the patient treatment plan (or other radiotherapy treatment attributes).

The medical professional may use the medical professional device (e.g., medical professional device 140*c*) as both a device to display results predicted by the analytics server 110*a* and in some cases as an electronic data source (e.g., electronic data source 120*b*) to train the machine learning models 111.

The analytics server 110*a* may recommend radiotherapy treatment attributes used for proton radiation, photon radiation, and electron radiation. In particular, analytics server 110*a* may utilize the methods and systems described herein to automatically learn and recommend field geometry attributes. The analytics server 110*a* may display the field geometry attributes on an end-user device 140*c*, medical computing device 162, and/or a medical professional device 120*b*. The analytics server 110*a* may also use the field geometry attributes via one or more downstream applications. For example, a downstream application may determine a treatment plan from the various recommended field geometry attributes. Using the field geometry treatment attributes, the downstream application may identify a treatment plan. The treatment plan may include information such as a dose distribution, radiation parameters such as beam angles, side effect prediction, organ and/or tumor segmentation, machine therapy attributes such as gantry position, beam blocking devices, treatment frequency, treatment timing, and treatment modalities, among others. Further, the analytics server 110*a* may transmit the field geometry attributes and other radiation parameters and/or treatment plan attributes to one or more other servers (e.g., clinic server 140*b*) such that a different device uses the field geometry attributes via one or more downstream applications. Additionally, or alternatively, the analytics server 110*a* (or other server) may adjust the configuration of one of end-user devices 140 (e.g., the end-user device 140*c*) based on the selected field geometry attributes.

The analytics server 110*a* may host a website accessible to users operating any of the electronic devices described herein (e.g., end users, medical professionals), where the content presented via the various webpages may be controlled based upon each particular user's role or viewing permissions. The analytics server 110*a* may be any computing device comprising a processor and non-transitory machine-readable storage capable of executing the various tasks and processes described herein. The analytics server 110*a* may employ various processors such as central processing units (CPU) and graphics processing unit (GPU), among others. Non-limiting examples of such computing devices may include workstation computers, laptop computers, server computers, and the like. While the system 100 includes a single analytics server 110*a*, the analytics server 110*a* may include any number of computing devices operating in a distributed computing environment, such as a cloud environment.

The analytics server 110*a* may execute software applications configured to display the electronic platform (e.g., host a website), which may generate and serve various webpages to each electronic data source 120 and/or end-user devices 140. Different users may use the website to view and/or interact with the recommended (optimized) results to select field geometry attributes for treatment.

Servers, such as analytics server 110*a*, server 120*c* and/or clinic server 140*b*, may use the selected recommended results in downstream processing (e.g., optimize one or more other radiation parameters and/or treatment plan attributes). For example, the analytics server 110*a* may use the selected field geometry attributes to optimize a dose distribution.

The analytics server 110*a* may be configured to require user authentication based upon a set of user authorization credentials (e.g., username, password, biometrics, cryptographic certificate, and the like). The analytics server 110*a* may access the system database 110*b* configured to store user credentials, which the analytics server 110*a* may be configured to reference in order to determine whether a set of entered credentials (purportedly authenticating the user) match an appropriate set of credentials that identify and authenticate the user.

The analytics server 110*a* may generate and host webpages based upon a particular user's role within the system 100. In such implementations, the user's role may be defined by data fields and input fields in user records stored in the system database of the clinic server 110*b*. The analytics server 110*a* may authenticate the user and may identify the user's role by executing an access directory protocol (e.g., LDAP). The analytics server 110*a* may generate webpage content that is customized according to the user's role defined by the user record in the system database 110*b*.

The analytics server 110*a* may receive patient data (e.g., medical images, height, weight, diagnosis, age, equipment, etc.) from a user or retrieve such data from a data repository, analyze the data, and display the results on the electronic platform. The analytics server 110*a* may preprocess the patient data (e.g., automatically segment the medical image). For instance, in a non-limiting example, the analytics server 110*a* may query and retrieve medical images from the database 120*d* and combine the medical images with segment data received from a medical professional operating the medical professional device 120*b* and/or medical device 160 to perform preprocessing on the medical image (e.g., segment the medical image).

The analytics server 110*a* may execute various machine learning models 111 (stored within the system database of the clinic server 140*b* or the analytics server 110*b*) to analyze the retrieved data. The analytics server 110*a* may then display the results to be interacted with via the electronic platform on the administrator computing device 150, the medical professional device 120b, medical computing device 162 and/or the end-user devices 140.

The electronic data sources 120 may represent various electronic data sources that contain, retrieve, and/or input data associated with a patient's treatment plan including patient data and treatment data. For instance, the analytics server 110a may use the clinic computer 120a, medical professional device 120b, server 120c (associated with a physician and/or clinic), and database 120d (associated with the physician and/or the clinic) to retrieve/receive data associated with the patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110a. Specifically, the end-user devices 140 may include clinic computer 140a, clinic server 140b, and a medical device professional 140c. Even though referred to herein as "end user" devices, these devices may not always be operated by end users. For instance, the clinic server 140b may not be directly used by an end user. However, the results stored onto the clinic server 140b may be used to populate various GUIs accessed by an end user via the medical professional device 140c.

The administrator computing device 150 may represent a computing device operated by a system administrator. The administrator computing device 150, along with the medical professional device 140c, medical professional device 120b, medical device computer 162, and the like, may be configured to display recommended field geometry attributes generated by the analytics server 110a (e.g., various analytic metrics determined during training of one or more machine learning models and/or systems); monitor various machine learning models 111 utilized by the analytics server 110a, electronic data sources 120, and/or end-user devices 140; review feedback; and/or facilitate training or retraining (calibration) of the machine learning models 111 that are maintained by the analytics server 110a.

The medical device 160 may be a radiotherapy machine (e.g., a linear accelerator, particle accelerator (including circular accelerators), or a cobalt machine)) configured to implement a patient's radiotherapy treatment. The medical device 160 may also include an imaging device capable of emitting radiation such that the medical device 160 may perform imaging according to various methods to accurately image the internal structure of a patient. For instance, the medical device 160 may include a rotating system (e.g., a static or rotating multi-view system). A non-limiting example of a multi-view system may include a stereo systems (e.g., two systems may be arranged orthogonally). The medical device 160 may also be in communication with a medical device computer 162 that is configured to display various GUIs discussed herein. For instance, the analytics server 110a may display the results predicted by the machine learning model 111 onto the medical device computer 162.

In operation, a medical professional may access an application executing on the medical professional device 120b and input patient data (e.g., patient information, patient diagnosis, radiation therapy radiation requirements and thresholds). The analytics server 110a then uses a patient identifier to query patient data (e.g., patient anatomy and/or medical images) from the electronic data sources 120. The analytics server may then identify a clinic associated with the patient (e.g., clinic performing the treatment) and retrieve one or more files associated with treatment templates and clinic rules. The analytics server 110a may then utilize the systems and methods described herein to generate recommended field geometry attributes to be displayed to (and interacted with) one or more medical professionals.

The analytics server 110a may be in communication (real-time or near real-time) with the computing device 162, end-user device 140 and/or electronic data sources 120, such that a server/computer hosting the medical device 160 can adjust the medical device 160 based on the recommended (or selected) field geometry attributes. For instance, the radiotherapy machine may adjust the gantry, beam blocking device (e.g., multi leaf collimator MLC), and couch based on field geometry attributes. The analytics server 110a may transmit instructions to the radiotherapy machines indicating any number or type of radiation parameters, beam angles, and/or treatment attributes to facilitate such adjustments.

The analytics server 110a may store machine learning models 111 (e.g., neural networks, random forest, support vector machines, or other deep learning models), that are trained to recommend radiotherapy treatment attributes (such as field geometry attributes) associated with a patient and a corresponding clinic, medical professional, guideline, instruction, or some combination thereof.

The analytics server 110a may train the machine learning models 111 using patient data and treatment data associated with patients who were previously treated. For instance, the analytics server 110a may receive patient data (e.g., physical attributes, diagnoses, medical images) and selected field geometry attributes treatment from one or more medical professionals, data sources 120 and clinic rules.

In an example, based on a patient data (e.g., a patient's BMI), a medical professional may determine to place the isocenter in the middle of a tumor and have a full arc gantry motion while the beam is on. As used herein, the isocenter (or the radiation isocenter) refers to the point in space where radiation beams intersect when the gantry rotates (e.g., half or full arcs) during the beam-on mode. However, for a second patient with a different BMI, the medical professional may determine to implement the same treatment by having a few fixed tube directions that are evenly distributed and attempt to avoid certain structure/organs of the patient's body. Therefore, different patients will result in different field geometry attributes (e.g., radiation beam angles), resulting in different implementations and procedures.

In another non-limiting example, a particular clinic-specific rule may indicate that a patient having physical attributes (e.g., height and weight) that satisfy a threshold will receive VMAT treatment in two arcs. As used herein, VMAT refers to a radiation therapy technique that delivers the radiation dose continuously as the treatment machine rotates. The clinic-specific rules may indicate that, unless expressly stated by the medical professional, the default radiotherapy methods should be VMAT radiation having two arcs. Another clinic may use other methods or may require fewer or more number of arcs. Therefore, different clinics will result in different field geometry attributes (e.g., number of VMAT arcs), resulting in different implementations and procedures.

Machine learning models 111 may be stored in the system database 110b and may correspond to individual radiotherapy clinics or otherwise different sets of radiotherapy machines (e.g., radiotherapy machines that are located at individual radiotherapy clinics, are located in different geographical regions, treat specific types of diseases (e.g., different types of cancer), treat specific genders, etc.). For example, the machine learning model 111 may be associated with an identifier indicating the radiotherapy clinic, set of radiotherapy machines, or a specific disease.

In various embodiments, machine learning models 111 use one or more deep learning engines to simulate an agent in a reinforcement learning model. Although exemplified using deep convolutional neural networks, it should be understood that any alternative and/or additional deep learning model(s) may be used to implement deep learning engines. The deep learning engines include processing pathways that are trained continually and/or trained during training phase. Once trained, deep learning engines may be used (e.g., by a medical professional) to select actions based on a policy and, for example, an epsilon value given an observed state.

One type of deep learning engine is a convolutional neural network (CNN). A CNN is a branch of neural networks and consists of a stack of layers each performing a specific operation, e.g., convolution, pooling, etc. Each intermediate layer receives the output of the previous layer as its input. The beginning layer is an input layer, which may be directly connected to an input image and may have a number of neurons equal to the number of pixels in the input image. The next set of layers are convolutional layers that present the results of convolving a certain number of filters with the input data and perform as a feature extractor. The filters, commonly known as kernels, are of arbitrary sizes defined by designers depending on the kernel size. Each neuron responds only to a specific area of the previous layer, called receptive field. The output of each convolution layer is considered as an activation map, which highlights the effect of applying a specific filter on the input. Convolutional layers may be followed by activation layers to apply non-linearity to the activation maps. The next layer can be a pooling layer that helps to reduce the dimensionality of the convolution's output. In various implementations, high-level abstractions are extracted by fully connected layers. The weights of neural connections and the kernels may be continuously optimized in the training phase.

Deep learning generally uses models to learn categories incrementally, e.g., learning lower-level categories before attempting to learn higher level categories. For example, a computer can be provided with a large dataset and, by using deep learning algorithms, can sort elements of the data into categories such as function, shape, etc. A "clustering" may occur based on similarity of data.

The aim of training is to train a deep learning engine to optimize a policy such that recommendations provided to a medical professional based on patient data are relevant and influenced by the medical professional's preferences, the clinic's preferences, the preferences in a certain geography/region, and the like. Training may involve optimizing policies by taking the gradient of an objective function (e.g., a reward function) to maximize a cumulative sum of rewards based on encouraging recommendations of radiotherapy treatment attributes that align with medical professional preferences, for instance.

A medical professional at a radiotherapy clinic may access an end-user device 140 located at the clinic or access an account associated with the clinic. The medical professional may provide an input at a user interface that causes the end user device 140 to transmit a request to access a machine learning model 111 that is associated with the clinic and/or the radiotherapy machines located within the clinic. The request may include an identifier associated with the machine learning model 111, the clinic, and/or the set of radiotherapy machines that the analytics server 110a may use as a key in a look-up table to identify the machine learning model 111. The analytics server 110a may receive the request and, in some cases, after authenticating the user, identify the machine learning model 111 via the identifier. The analytics server 110a may transmit the identified machine learning model 111 to the end-user device 140 or send an alert indicating the end-user device is authorized to access the model(s) 111. Upon receipt or access to the machine learning model 111, the end user device 140 may perform the systems and methods described herein to train or retrain the machine learning model 111 to predict (and improve or optimize) field geometry attributes.

Figure 2:
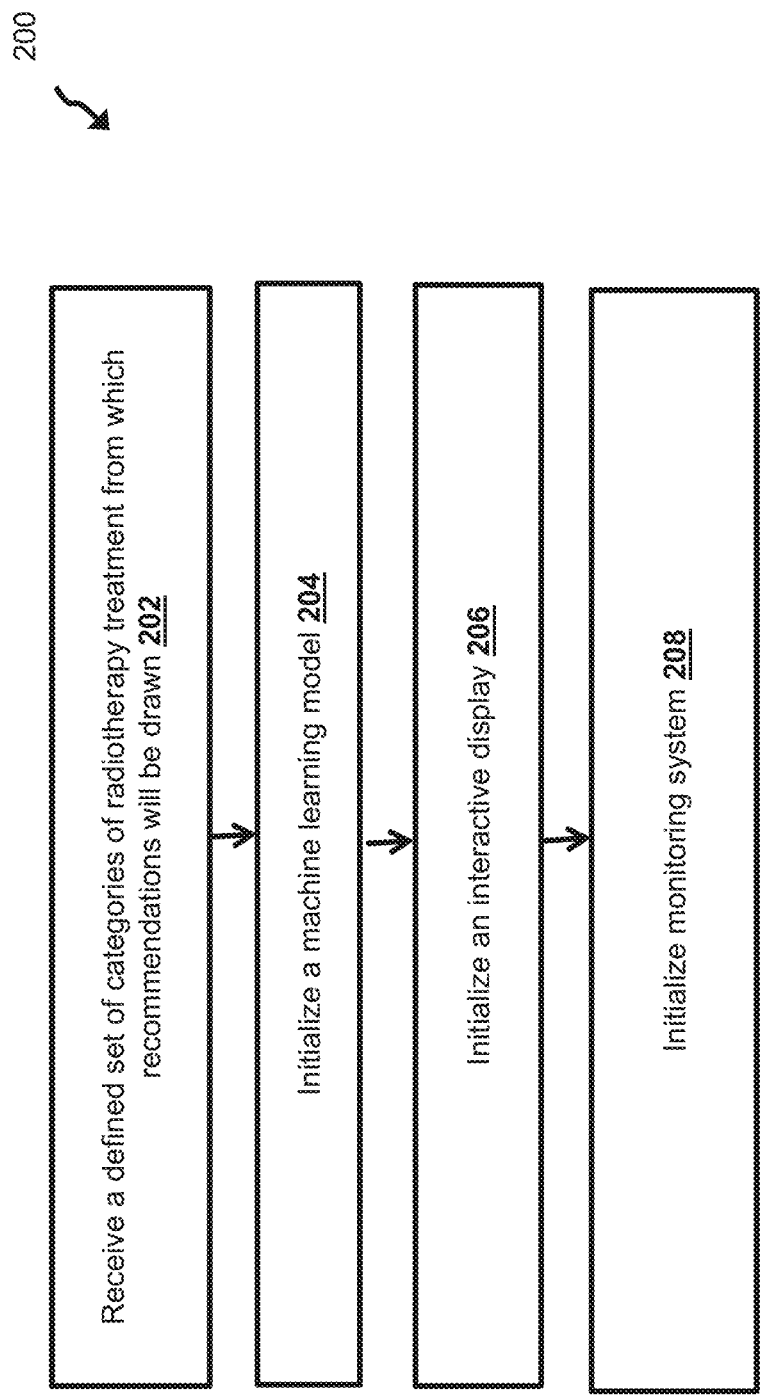
FIG. 2 illustrates a flow diagram of an initialization process executed prior to executing a radiotherapy treatment attribute recommendation system, according to an embodiment.

FIG. 2 illustrates a flow diagram of an initialization process executed prior to executing a radiotherapy treatment attribute recommendation system, according to an embodiment. While the systems and methods described herein relate to an initialization process executed prior to executing a radiotherapy treatment attribute recommendation system (and specifically, recommending field geometry attributes), it should be appreciated that the systems and methods described herein relate to other areas of radiation oncology and radiation therapy treatment planning where decisions are to be made from a set of pre-defined options. The method 200 may include steps 202-208. However, other embodiments may include additional or alternative steps, or may omit one or more steps altogether. The method 200 is described as being executed by a server, such as the analytics server described in FIG. 1. However, one or more steps of method 200 may be executed by any number of computing devices operating in the distributed computing system described in FIG. 1. For instance, one or more computing devices may locally perform part or all of the steps described in FIG. 2.

In step 202, the analytics server receives a defined set of categories of radiotherapy treatment from which recommendations will be drawn. FIG. 3 illustrates example categories of radiotherapy treatment (e.g., field geometry categories) and radiotherapy treatment attributes (e.g., radiotherapy treatment attribute options such as field geometry attributes).

As shown, the example categories of radiotherapy treatment correspond to categories of field geometries. Cell 301 indicates the radiation therapy treatment technique category, which includes radiotherapy treatment attributes (or field geometry attributes) in cells 302 and 303. That is, the two field geometry attribute options for the field geometry category "radiation therapy treatment technique" are VMAT and IMRT. As shown, the VMAT and IMRT field geometry attributes may further be broken down into other field geometry options. For example, the VMAT field geometry attribute may include field geometry attribute options such as standard VMAT (two full arcs), complex VMAT (two partial arcs), complex VMAT (three arcs), complex VMAT (four arcs, and the like. Similarly, cell 310 indicates the couch rotation category, which is an example of a field geometry category (e.g., a specific example of a radiotherapy treatment category). The couch rotation category includes radiotherapy treatment attribute options in cell 312. Cell 320 indicates the collimator angle settings, which includes the radiotherapy treatment attribute options in cell 322.

A medical professional may input the categories and/or options of radiotherapy treatment. Additionally, or alternatively, the radiotherapy treatment categories and/or options of radiotherapy treatment attributes may be determined by the clinic, based on the geography, the radiotherapy machine, automatically (e.g., using one or more other models/algorithms) and the like.

Figure 4:
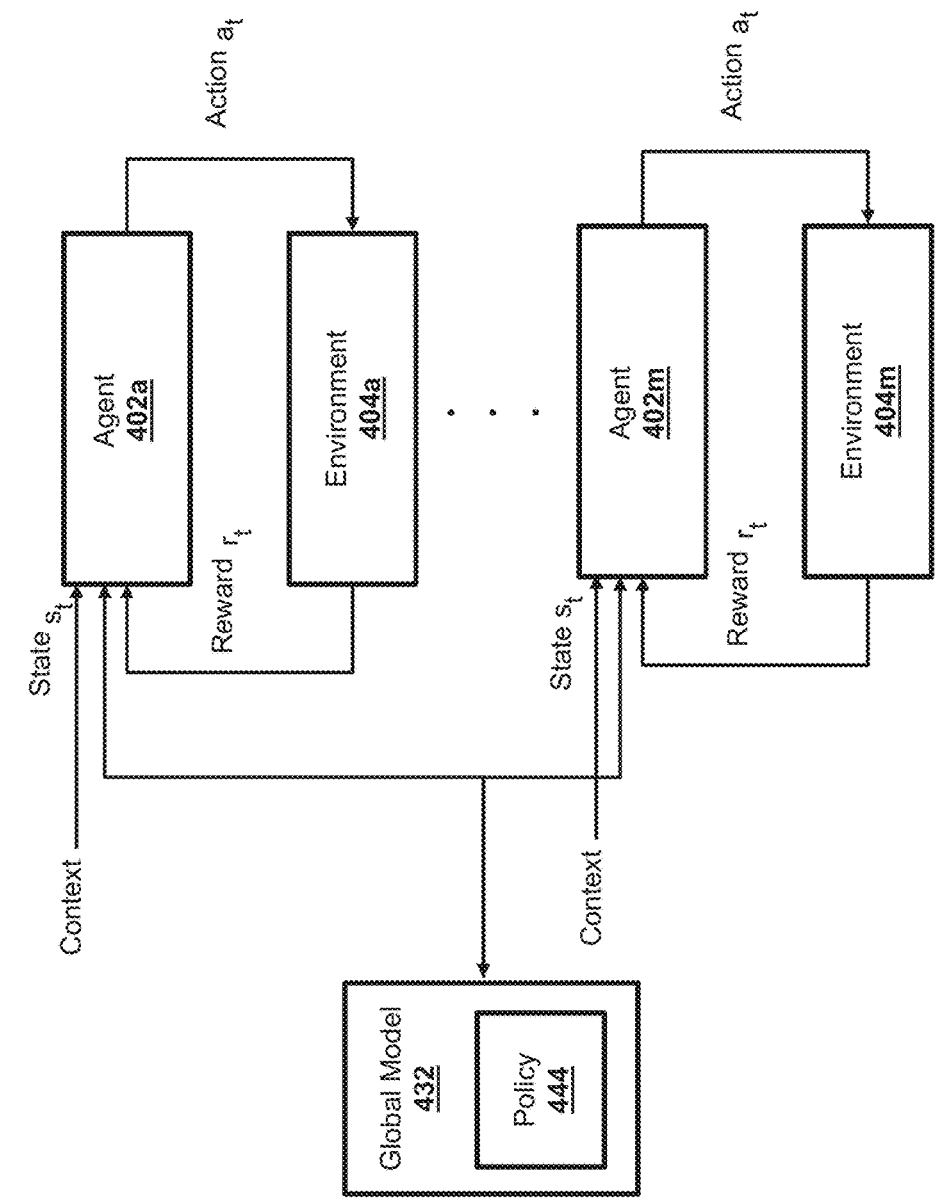
FIG. 4 illustrates a reinforcement learning model, according to an embodiment.

In step 204, the analytics server may initialize a machine learning model. In some implementations, the machine learning model may be a neural network trained using reinforcement learning. FIG. 4 illustrates a reinforcement learning model 400, according to an embodiment. The reinforcement learning model 400 (or contextual bandit, contextual bandit reinforcement learning model) is one example of the field geometry recommendation system executed by the analytics server (e.g., recommendation engine 724 in FIG. 7B). Agents use the reinforcement learning method to train themselves/AI model to recommend a field geometry attribute (or radiotherapy treatment attribute). For example, an agent may use an actor-critic approach to learn.

The model 400 is implemented to recommend radiotherapy treatment attributes (specifically, field geometry attributes) of various radiotherapy treatment categories based on preferences of medical professionals, clinics, institutional guidelines, geography/regions, and/or some combination thereof. The context of the framework is based on the patient's geometry and/or patient data. The available actions in the solution space are the set of radiotherapy treatment attributes (e.g., field geometry attributes) recommended to the medical professional. The reward is based on whether the recommended radiotherapy treatment attributes were accepted by medical professional.

More specifically, in reinforcement learning, an agent 402a to 402m (collectively referred to herein as agent 402) interacts with an environment 404 (e.g., environment 404a to 404m respectively). The agents 402 refer to the learner or trainer (e.g., the analytics server training the AI model or the AI model itself). Each recommendation task t (e.g., one-step reinforcement learning) the agent 402 observes a state $s_t$ based on a context (e.g., input patient data) and selects an action from a set of actions using a policy 444. The analytics server may train the neural network using contextual bandit learning because each state $s_t$ is independent from the next state $s_{t+1}$. That is, the contextual bandit method is one-step reinforcement learning.

The agents 402 ingest patient data received by the model 400. In some implementations, the analytics server transforms and/or pre-processes the patient data. For example, the dimensionality of the patient data may be reduced before the agents 402 receive the patient data.

The goal of the agent 402 is to continuously learn and refine policy 444 to recommend acceptable field geometry attributes to the medical professional. The learning occurs as the agent 402 maximizes its cumulative reward. The agent 402 may receive a positive reward when the medical professional accepts the recommendation determined by the model 400. Accordingly, the policy 444 and action resulting may be encouraged based on the patient data context. The analytics server may determine whether the medical professional accepted the recommendation based on monitoring the medical professional's inputs.

Referring back to FIG. 2, in step 206, the analytics server initializes an interactive display. The interactive display may be interacted with using a mouse/keyboard (or other hardware), touch screen, by tracking the medical professional's eyes, using voice activated prompts, and the like. The interactive display may be any display that may be utilized by a medical professional while the medical professional is setting up the patient (or planning to set up the patient). For example, the interactive display may be a display on the radiotherapy machine (e.g., medical device 160 in FIG. 1), a computer associated with the medical device (e.g., medical device computer 162 in FIG. 1), an end-user device (e.g., end-user devices 140 in FIG. 1) or electronic data source (e.g., electronic data source 120 in FIG. 1). The analytics server may be configured to receive inputs from the interactive display. The interactive display is an example of one method of receiving medical professional preferences. Receiving medical professional preferences may facilitate the training of the machine learning model (e.g., reinforcement learning model 400 in FIG. 4)

In step 208, the analytics server initializes a monitoring system. The monitoring system may be any system configured to track the medical professional's interactions with the interactive display. In some implementations, the monitored interactive data may be stored (e.g., in server 120c and/or clinic server 140b in FIG. 1). In some implementations, the monitored interactive data may be converted from one type of data into another type of data, scaled, transformed, and the like. In some implementations, in addition to the monitored interactive data, the analytics server may store the context and the interactive data. For example field geometry attributes selected by a medical professional may be mapped to patient data.

In some implementations, the policy of the machine learning model (e.g., policy 444 in FIG. 4) is trained based on monitoring the medical professional over time. That is, the policy is trained on field geometry attributes determined by the medical professional. As the medical professional is interacting with the interactive display and selecting radiotherapy treatment attributes (and specifically, field geometry attributes), and the analytics server monitors the medical professional's inputs, the agents in the machine learning model (e.g., agents 402 in FIG. 4) may observe the medical professional interactions to determine, refine and train a policy.

In other implementations, before the machine learning model is trained, the analytics server may assign probabilities for categories of radiotherapy treatment and/or for radiotherapy treatment attributes. Accordingly, radiotherapy treatment attributes may be associated with an initial bias. For example, if a majority of patients receive a standard VMAT configuration, then the analytics server may assign the field geometry attribute associated with a standard VMAT configuration a higher probability such that the policy is more likely to select the standard VMAT configuration action. Additionally, or alternatively, the analytics server may assign a homogeneous probability distribution for each radiotherapy treatment attribute.

Referring back to FIG. 4, the policy 444 maps states (and observations) to actions. The policy 444 gives the probability of taking a certain action when the agent 402 is in a certain state. The possible set of actions may include selecting radiotherapy treatment attributes and radiotherapy treatment categories. For example, the possible set of actions may include field geometry attributes for each category of field geometries as shown in FIG. 3.

The possible set of actions (e.g., action space) may be arbitrarily defined and depend on the solution space considerations. For example, the solution space may be discretized such that the recommended (or predicted) radiotherapy treatment attributes are binary classifications. For instance, field geometry attributes defined by the action space may include VMAT or IMRT, VMAT standard or VMAT complex, IMRT standard or IMRT complex, rotate couch or do not rotate couch, default collimator angle or non-default collimator angle. The action space may also include multiclass classifications of treatment attribute options (e.g., VMAT one arc, VMAT two arcs, VMAT three arcs, and the like).

The action space may also include more complex schemes such as recommending multiple categories of radiotherapy treatment. For example, the action space may include actions such as recommend VMAT with couch rotation, recommend VMAT with two arcs where the two arcs are partial arcs, among others.

In other examples, the solution space may be continuous rather than discrete. For example, the action space may include actions such as "recommend x arcs" where the x number of arcs may vary throughout training, vary based on the criteria, and the like. The action space may also include actions such as "rotate couch x degrees" or "move collimator angle x degrees." In the event a continuous solution space is implemented, the agents 402 may need to train for longer.

Agents 402 may select an action based on the value of taking each action, where the value of selecting the action is defined as the expected reward received when taking that action from the possible set of actions. Agents 402 may select actions based on exploratory actions and exploitation actions. The contextual bandit agent is continuously optimizing its current and future performances as it balances exploitation and exploration and aims to generalize to new contexts. An exploratory action improves an agent's knowledge about an action by using the explored action in a sequence resulting in a reward calculation. An exploratory action is an action unrestricted by prior knowledge. An exploitation action is a "greedy" action that exploits the agent's 402 current action-value estimates. For example, when the epsilon indicates the exploration action, the policy 444 may direct the agent 402 to select a random action. In contrast, when the epsilon indicates the exploitation action, the policy 444 may direct the agent 402 to select an action that has previously received a reward given one or more similar patient data characteristics (e.g., same diagnosis, same BMI, same age, same gender, same combination of patient data characteristics, and the like).

In some embodiments, the analytics server may inject parameter noise into the model 400. Parameter noise may result in greater exploration and more successful model 400 by adding noise to the parameters of the policy selection.

Using epsilon-greedy action selection, for example, the agent 402 balances exploratory actions and exploitation actions. The agent 402 may select an epsilon value and perform an exploitation action or an exploratory action based on the value of the epsilon and one or more exploitation and/or exploration thresholds. The agent 402 may randomly select an epsilon value, select an epsilon value from a predetermined distribution of epsilon values, select an epsilon value in response to the environment 404, select an epsilon value in response to one or more criteria, select an epsilon value in response to the number of training epochs, select an epsilon value in response to one or more gradients, and the like.

In some embodiments, as training progresses, exploitation actions may be leveraged to refine training the experts. For example, the analytics server may revise the epsilon value (or epsilon selection method) such that the likelihood of the exploration action is higher or lower than the likelihood of the exploitation action. Additionally, or alternatively, the analytics server may revise the exploitation action threshold and/or the exploration action threshold.

Agents 402 may also select an action using policy 444. The policy 444 may be a global policy such that the agents 402 share a common policy. The policy 444 is tuned based on the value of taking each action, where the value of selecting the action is defined as the expected reward received when taking that action from the possible set of actions. In some configurations, the analytics server may update the policy 444 using agents operating in other servers (e.g., via federated learning).

The policy 444 may be stored in a global model 432. Using a global model 432 allows each agent 402 to have a more diversified training dataset and eliminates a need for synchronization of models associated with each agent 402. The global model 432 with agents 402a to 402m may produce an m-dimensional output. In other configurations, there may be models associated with each agent (e.g., m models), and each agent may calculate a reward using a designated machine learning model. Each agent may tune its own policy. The policy class of the agent may be represented by a general linear classifier, support vector machine, random forest, or another machine learning model (e.g., deep neural network). If generalized linear methods are used in the agent design, the online usage of contextual bandits (including continual training) may be fast.

The output of the agent may be a softmax layer with classes indicating the field geometry attribute options (or other radiotherapy treatment attributes). The softmax function is used to score each field geometry attribute. The analytics server may select a recommendation to the medical professional by comparing a recommendation score associated with each field geometry attribute. In some implementations, the analytics server may display the top-n recommendations, all radiotherapy treatment attribute options ranked in order of most recommended to least recommended, or only one recommendation. In other implementations, the analytics server may determine to display recommendations by comparing the recommendation scores associated with a recommendation to other recommendation scores and/or one or more thresholds. For example, in the event that a threshold number of agents 402 select the same recommendation, the analytics server may determine to display the selected recommendation.

In response to selecting an action (or multiple actions), the agent 402 may receive feedback, indicating how the action affected the environment 404. In some configurations, the agent 402 determines the feedback. In other configurations, the analytics server may provide feedback to an agent 402.

Each iteration (or after multiple iterations and/or steps), the agent 402 selects a policy 444 (and an action) based on the current state $s_t$ (e.g., the context, the patient data), the epsilon value, and the agent 402 (or the machine learning model) calculates a reward. Each iteration, the agent 402 (or machine learning model) learns to perform better as can be seen in the increase of the rewards (e.g., an iterative summation of rewards).

Figure 5:
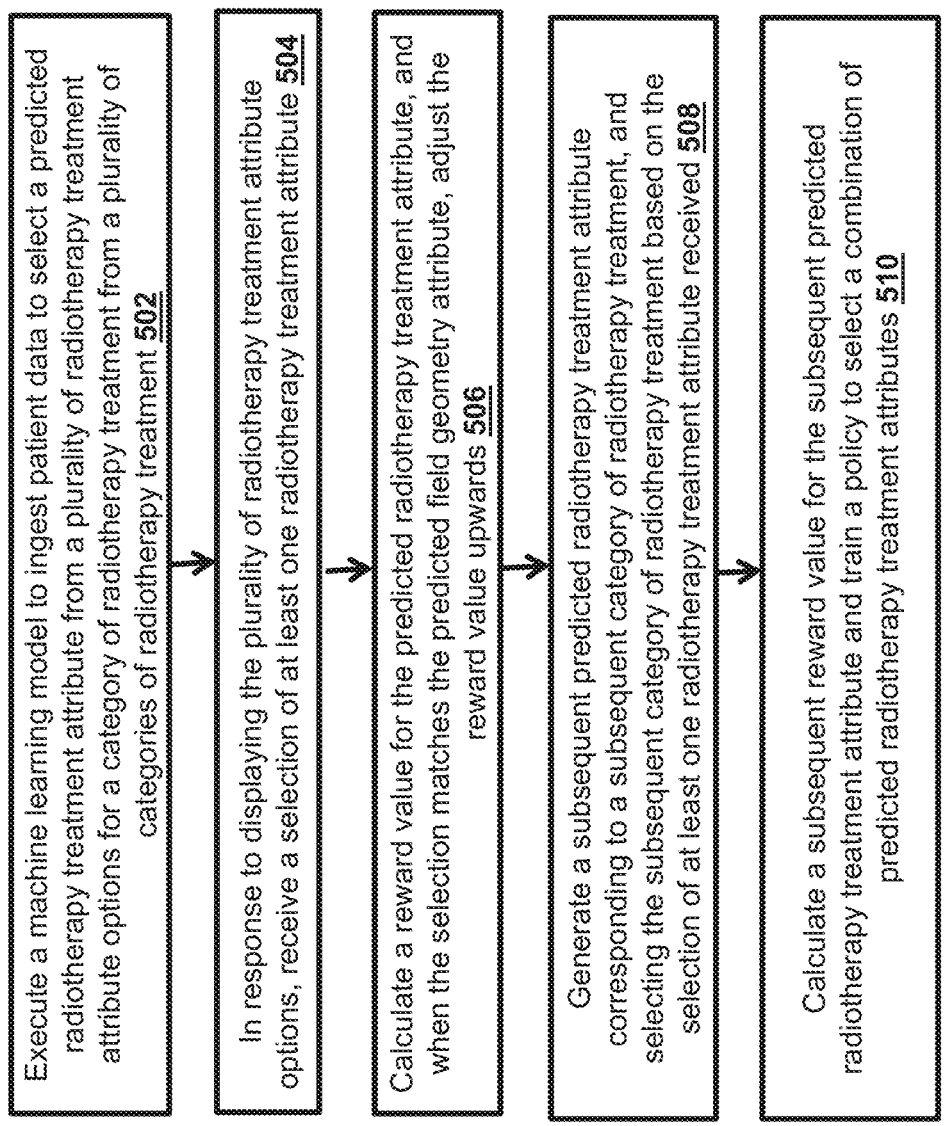
FIG. 5 illustrates a flow diagram of a process executed in a radiotherapy treatment attribute recommendation system, according to an embodiment.

FIG. 5 illustrates a flow diagram of a process executed in a radiotherapy treatment attribute recommendation system, according to an embodiment. The method 500 includes steps for determining a revised (optimized, improved, modified, identified, selected, and/or predicted) field geometry attribute, set of field geometry attributes, or other radiotherapy treatment attributes, according to an embodiment. In operation, based on ingested (or received) patient data, the analytics server recommends one or more radiotherapy treatment attributes that a medical professional can accept or reject. The analytics server may record whether the medical professional accepted or rejected the recommendation such that the machine learning model continues to learn the preferences of the medical professional (or clinic).

As described herein, inputs and outputs may be described in the singular (e.g., ingest a medical image or output a recommended field geometry attribute). It should be appreciated that multiple inputs (e.g., medical images and corresponding PTV/OAR structures in the medical images) and multiple outputs (e.g., a set of field geometry attributes (e.g., a template), a set of radiotherapy treatment attributes, and the like) are considered. In an example, a treatment plan may consist of multiple radiotherapy treatment attributes including dose distribution, beam angles and other field geometry attributes such as couch angle, type of treatment (VMAT or IMRT), and the like. The method 500 may include steps 502-510. However, other embodiments may include additional or alternative steps, or may omit one or more steps altogether.

The method 500 is described as being executed by an analytics server, such as the analytics server described in FIG. 1. The analytics server may employ one or more CPUs and GPUs to perform one or more steps of method 500. The CPUs and/or GPUs may be performed in part by the analytics server and in part by one or more other servers and/or computing devices. The servers and/or computing devices employing the CPUs and GPUs may be local and/or remote (or some combination). For example, one or more virtual machines in a cloud may employ one or more CPUs and GPUs to perform one or more steps of method 500. A hybrid CPU and GPU implementation may improve the speed associated with training a machine learning model to recommend radiotherapy treatment attributes (including field geometry attributes). However, one or more steps of method 500 may be executed by any number of computing devices operating in the distributed computing system described in FIG. 1. For instance, one or more computing devices may locally perform part or all of the steps described in FIG. 5. Moreover, an "agent," referring to the learner or the trainer (e.g., the analytics server training the machine learning model or the machine learning model itself), may perform one or more steps discussed herein.

In step 502, the analytics server executes a machine learning model to ingest patient data (e.g., patient medical files, patient medical images) to select a predicted radiotherapy treatment attribute from a plurality of treatment attribute options for a category of radiotherapy treatment from a plurality of categories of radiotherapy treatment.

The analytics server may receive the patient data from one or sources (e.g., user devices such as physician device 120*b*, end-user devices 140 including the radiotherapy machine 140*d*, databases 110*b*, and electronic data sources 120 in FIG. 1). For instance, the analytics server may query one or more databases to identify medical data associated with the patient. The analytics server may query data associated with the patient's anatomy, such as physical data (e.g., height, weight, and/or body mass index) and/or other health-related data (e.g., blood pressure or other data relevant to the patient receiving radiation therapy treatment). The analytics server may also retrieve data associated with current and/or previous medical treatments received by the patient (e.g., data associated with the patient's previous surgeries).

The analytics server may analyze the data received and may generate additional queries accordingly. For instance, the analytics server may retrieve data associated with one or more medical (or other) devices needed for the patient. The analytics server may retrieve data indicating that the patient suffers from a respiratory medical condition. As a result, the analytics server may generate and transmit a query to one or more electronic data sources to identify whether the patient uses/needs a ventilator or other medical equipment.

If necessary, the analytics server may also analyze the patient's data records to identify the needed patient attributes. For instance, the analytics server may query a database to identify the patient's body mass index (BMI). However, because many medical records are not digitalized, the analytics server may not receive the patient's BMI value using simple query techniques. As a result, the analytics server may retrieve the patient's electronic health data and may execute one or more analytical protocols (e.g., natural language processing) to identify the patient's body mass index. In another example, if the analytics server does not receive PTV and/or OAR data, then the analytics server may execute various image recognition protocols and segmentation protocols to identify the PTV and/or OAR data in various medical images (e.g., planning images, simulation images, and diagnostic images). For example, the analytics server may automatically segment and/or pre-process various medical images using trained machine learning models. The analytics server may transform or otherwise convert the medical image into a point cloud representation of structures (e.g., PTVs and/or OARs) in the medical images. An automatic image segmentation module may automatically segment PTVs and/or OARs in medical images. The medical images may be segmented, or otherwise analyzed to identify different contrasts in the medical image. The machine learning models may be trained to segment medical images and generate contours on the medical images, segmenting the medical image and identifying one or more PTVs and/or OARs.

In some configurations, the medical images may be two-dimensional (2D). In other configurations, the medical images may be three-dimensional (3D). If the medical images are 2D, the analytics server may convert the 2D images into 3D images (e.g., using triangulation protocols, photogrammetry). Medical images may include CT scans, 4D CT scans, MRIs, and X-ray images, among others.

The analytics server may select a predicted radiotherapy treatment attribute from various radiotherapy treatment attributes using a machine learning model (e.g., the machine learning model initialized in step 204 in FIG. 2). For example, based on the patient data (e.g., the context), the machine learning model may recommend IMRT.

Additionally, or alternatively, the analytics server may use statistical relational learning with Markov Logic Networks to select a predicted radiotherapy treatment attribute, as described in U.S. application Ser. No. 17/029,799, which is incorporated by reference herein in its entirety. For example, a machine learning model may be trained based on previously performed radiation therapy treatments and corresponding patient data to in view of clinic-specific preferences. The machine learning model may identify clinic-specific preferences to implement treatment of a patient. A logical network computer model configured to determine field geometry attributes associated with the patient's treatment employs a set of predefined rules expressed in logical sentences for a particular clinic to determine a field geometry attribute for each patient.

Figure 6:
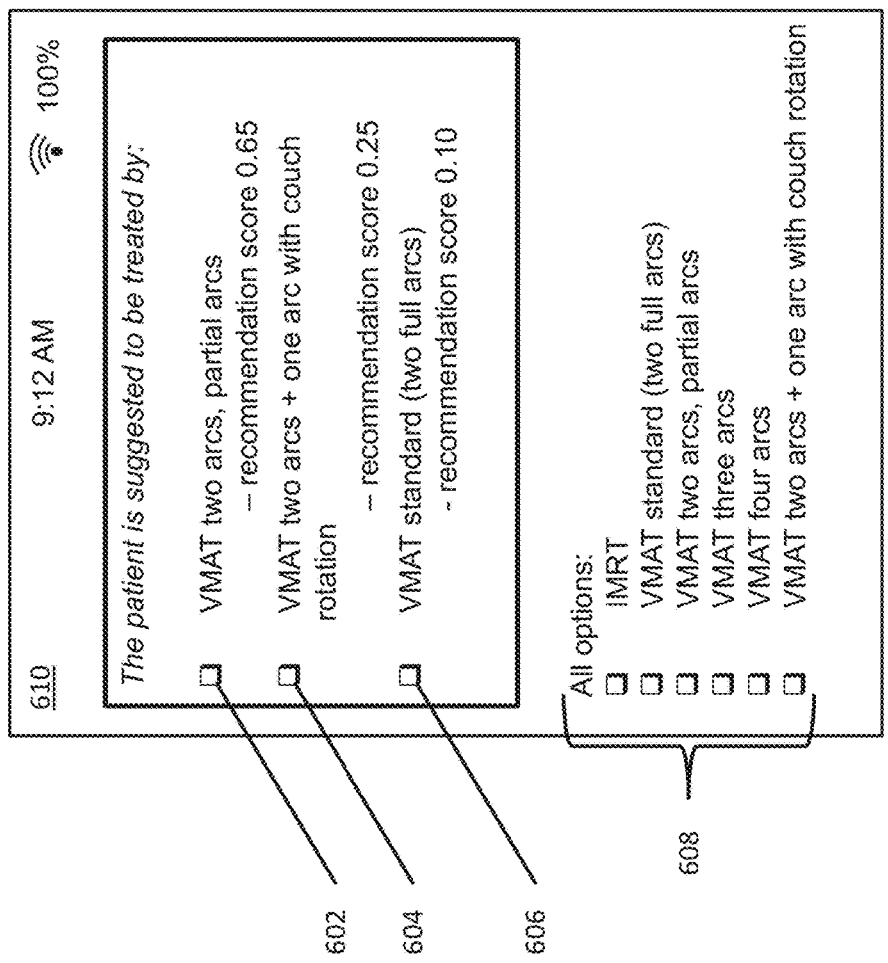
FIG. 6 illustrates an interactive display providing field geometry attribute recommendations to a medical professional, according to an embodiment.

FIG. 6 illustrates an example interactive display 600 providing field geometry attribute recommendations to a medical professional. As shown, the interactive display provides the medical professional with three recommendations 602, 604, and 606. Each recommendation is associated with a recommendation score. The recommendation score may be an indication of the agent's confidence (e.g., agent 402 in FIG. 4) in recommending the field geometry attribute to the medical professional. In some embodiments, the analytics server does not display the recommendation score on the interactive display 610.

As discussed herein, the agent recommends field geometry attributes according to the policy (e.g., policy 444 in FIG. 4) and context (e.g., patient data). The analytics server displays the recommended field geometry attributes on the interactive display 610. As shown, the top three recommendations (e.g., recommendation 602, recommendation 604, and recommendation 606) are displayed.

The recommendations 602, 604, and 606 illustrate example recommendations of field geometry attribute options of a particular field geometry attribute category. That is, the interactive display 610 is displaying predicted radiotherapy treatment attributes from a variety of radiotherapy treatment attribute options for a category of radiotherapy treatment from various categories of radiotherapy treatment.

Referring back to FIG. 5, in step 504, in response to displaying the treatment attribute options (e.g., recommendations 602, 604, and 606 in FIG. 6), the analytics server may receive a selection of at least one attribute. As discussed herein, the analytics server may receive interaction information in various forms (e.g., mouse/keyboard (or other hardware) data, touch data, eye-tracking data, audio commands, and the like). Referring back to FIG. 6, the medical professional may select a recommended field geometry attribute by interacting with the interactive display 610 (e.g., selecting a box associated with a recommendation). Additionally or alternatively, the medical professional may select a field geometry attribute that was not recommended out of the field geometry attribute options 608.

Referring back to FIG. 5, in step 506, the analytics server may calculate a reward value for the predicted radiotherapy treatment attribute. When the medical professional's selection matches the predicted field geometry attribute, the reward value may be adjusted upwards.

Referring back to FIG. 4, one goal of reinforcement learning is to determine a policy 444 that maximizes the cumulative set of rewards, determined via the reward function. The agent 402 learns (e.g., reconfigures its policy 444) by taking actions, evaluating feedback, and analyzing the rewards received.

The analytics server may determine a reward based on monitoring the inputs of the medical professional (e.g., step 506 in FIG. 5). For example, the reward may be binary (no reward or reward). In response to the medical professional selecting any displayed field geometry attribute recommendation (or other radiotherapy treatment attribute) determined by the agents 402, the agents 402 may receive a reward. In contrast, if the medical professional does not select a recommended field geometry attribute (or other radiotherapy treatment attribute), then the agents 402 may not receive a reward.

The analytics server may also calculate the reward using a reward function. A reward function can include, for example, functions based on the observed state $R(s_t)$, and/or functions based on the observed state and the action taken by the agent 402 $R(s_t, a_t)$. The reward may also be based on the probability of the recommendation.

The analytics server weighs policies based on the rewards determined at each step (or series of steps, or batches) such that certain policies (and actions) are encouraged and/or discouraged in response to the environment 404 being in a certain state. The machine learning model may be configured to learn (or revise the policy) after a predetermined number of medical professional recommendations are selected. The policies are optimized by taking the gradient of an objective function (e.g., a reward function) to maximize a cumulative sum of rewards at each step, or after a predetermined number of steps (e.g., a delayed reward).

In some configurations, the rewards at each step may be compared (e.g., on an iterative basis) to a baseline. The baseline may be an expected performance (e.g., the selection recorded by the medical professional), or an average performance (e.g., the average selection recorded by the medical professional, the average selection recorded by the medical professional for patients with similar patient data characteristics (e.g., similar context)). Evaluating a difference between the baseline and the reward is considered evaluating a value of advantage (or advantage value). The value of the advantage indicates how much better the reward is from the baseline (e.g., instead of an indication of which actions were rewarded and which actions were penalized). In some implementations, the reward may be the same as the baseline.

Referring back to FIG. 5, in step 508, the analytics server may generate a subsequent predicted radiotherapy treatment attribute corresponding to a subsequent category of radiotherapy treatment. The analytics server may select the subsequent category of radiotherapy treatment based on the selection of the radiotherapy treatment attribute.

For example, in response to receiving the medical professional's selection of the radiotherapy treatment attribute (e.g., a recommended radiotherapy treatment attribute such as recommendations 602, 604, and 606 in FIG. 6 or a radiotherapy treatment attribute that was not recommend such as radiotherapy treatment attribute options 608 in FIG. 6), the machine learning model (e.g. asynchronous advantage actor critic contextual bandit reinforcement learning model 400 in FIG. 4) may subsequently recommend a second radiotherapy treatment attribute. The machine learning model may recommend a radiotherapy treatment attribute in a different category of radiotherapy treatment. For example, in response to receiving the medical professional's selection of IMRT (e.g., a field geometry attribute in a first field geometry category), the machine learning model may recommend to rotate the couch (e.g., a field geometry attribute in a second field geometry category).

In some implementations, the subsequent category is selected using a workflow for radiotherapy treatment. The workflow may be the stages of work associated with treating a patient using a radiotherapy machine. For example, a standard workflow may include selecting a radiation therapy treatment technique before selecting whether the couch should be rotated. It may not be feasible and/or efficient for a medical professional to select a start/stop collimator angle if the radiation therapy treatment technique is not selected yet. The workflow may be a standard workflow, a workflow defined by the clinic, a workflow defined by the medical professional, or some combination thereof.

The machine learning model may also recommend an additional radiotherapy treatment attributes in the same radiotherapy treatment category. For example, if the machine learning model recommends a complex VMAT field geometry attribute, the machine learning model may further recommend four arcs.

In other implementations, the machine learning model may recommend a set of radiotherapy treatment attributes. That is, instead of subsequently predicting radiotherapy treatment attributes based on the selection of the received radiotherapy treatment attribute, the analytics server may display a set of recommended radiotherapy treatment attributes. For example, the interactive display may display one or more radiotherapy treatment attribute options for a first category of radiotherapy treatment and one or more second radiotherapy treatment attribute options for second category of radiotherapy treatment. More specifically, one or more agents may recommend a complex VMAT (four arc) (e.g., a field geometry attribute associated with a first category of radiotherapy treatment) and also recommend a start angle and stop angle of the collimator (e.g., a second field geometry attribute associated with a second category of radiotherapy treatment).

In some implementations, the subsequent predicted radiotherapy treatment attribute may be a radiotherapy treatment attribute associated with a new patient. For example, the machine learning model may ingest data associated with a second patient (e.g., a new context, different patient data). The machine learning model may learn the preferences of the medical professional (or the clinic, geography, or institutional guidelines) based on the reward determined in step 506 such that the policy dictating the action is encouraged or discouraged for subsequent patients.

Accordingly, the subsequent predicted radiotherapy treatment attribute is recommended by the machine learning model given the context of the new patient. As discussed herein, the analytics server displays the subsequently predicted radiotherapy treatment attribute. The displayed subsequently predicted radiotherapy treatment attribute may be the radiotherapy treatment attribute from the radiotherapy treatment attribute options that received the highest recommendation score, the radiotherapy treatment attribute that the majority (or some other fraction) of the agent's selected, the radiotherapy treatment attribute that is predicted to produce a higher reward than other treatment attribute options, and the like.

In step 510, the analytics server may calculate a subsequent reward value for the subsequent predicted radiotherapy treatment attribute. The analytics server may train a policy to select a combination of predicted radiotherapy treatment attributes that generate a cumulative reward value that satisfies a threshold. For example, the analytics server may select the predicted radiotherapy treatment attribute and subsequently predicted radiotherapy treatment attribute based on a policy that maximizes the reward value of the combination of the predicted radiotherapy treatment attributes. For instance, the cumulative reward value satisfying the threshold indicates that the cumulative reward value is higher than other cumulative reward values associated with other possible predicted radiotherapy treatment attributes.

Figure 7A:
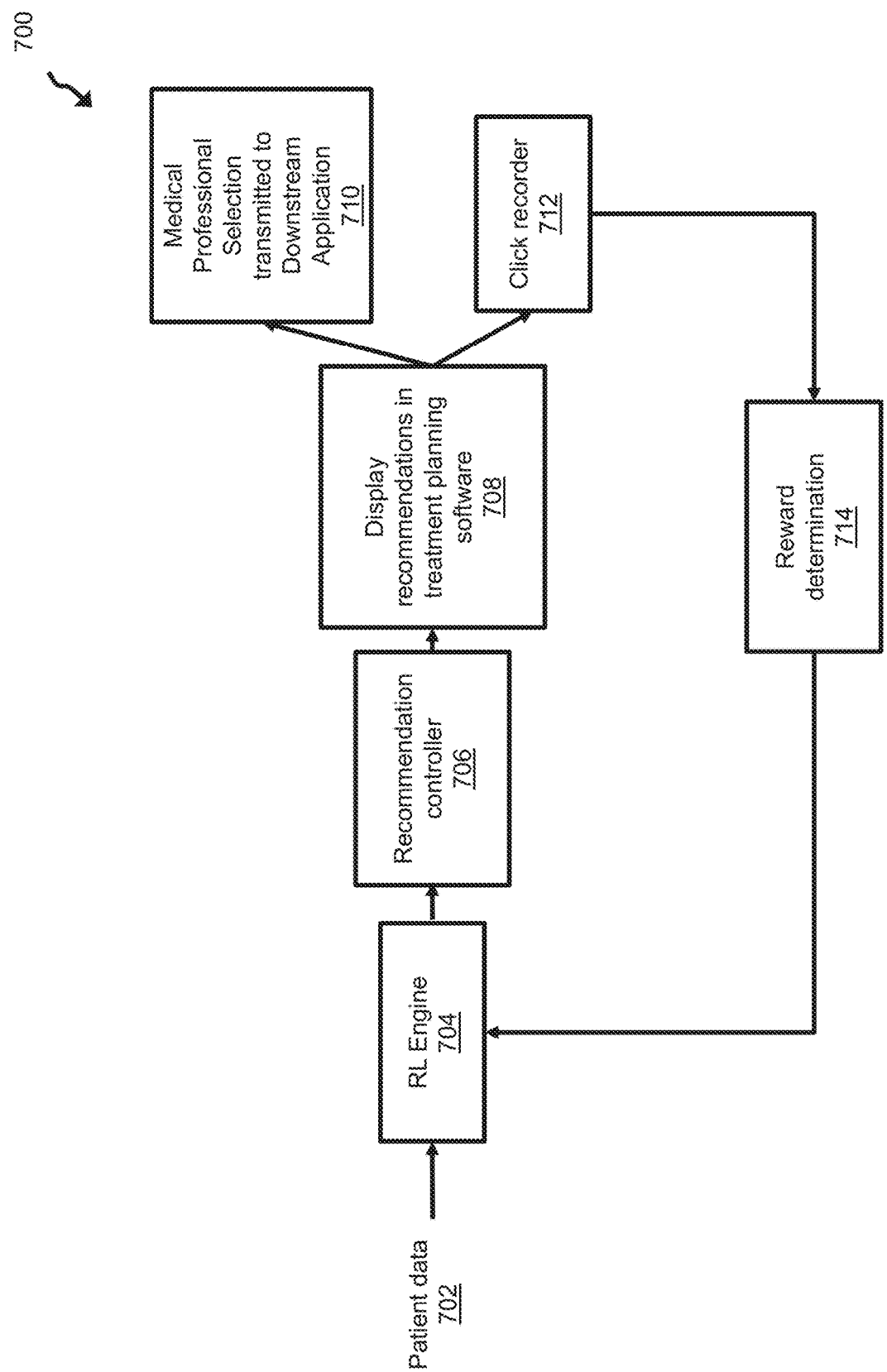
FIG. 7A illustrates a non-limiting visual example of a workflow utilizing the methods and systems described herein, according to an embodiment.

FIG. 7A illustrates a non-limiting visual example of a workflow 700 utilizing the methods and systems described herein, according to an embodiment. In this example, the analytics server receives patient data and provides recommendations of categories of radiotherapy treatment (and radiotherapy treatment attributes). Specifically, the analytics server provides recommendations of field geometry attributes from field geometry attribute options.

Figure 7B:
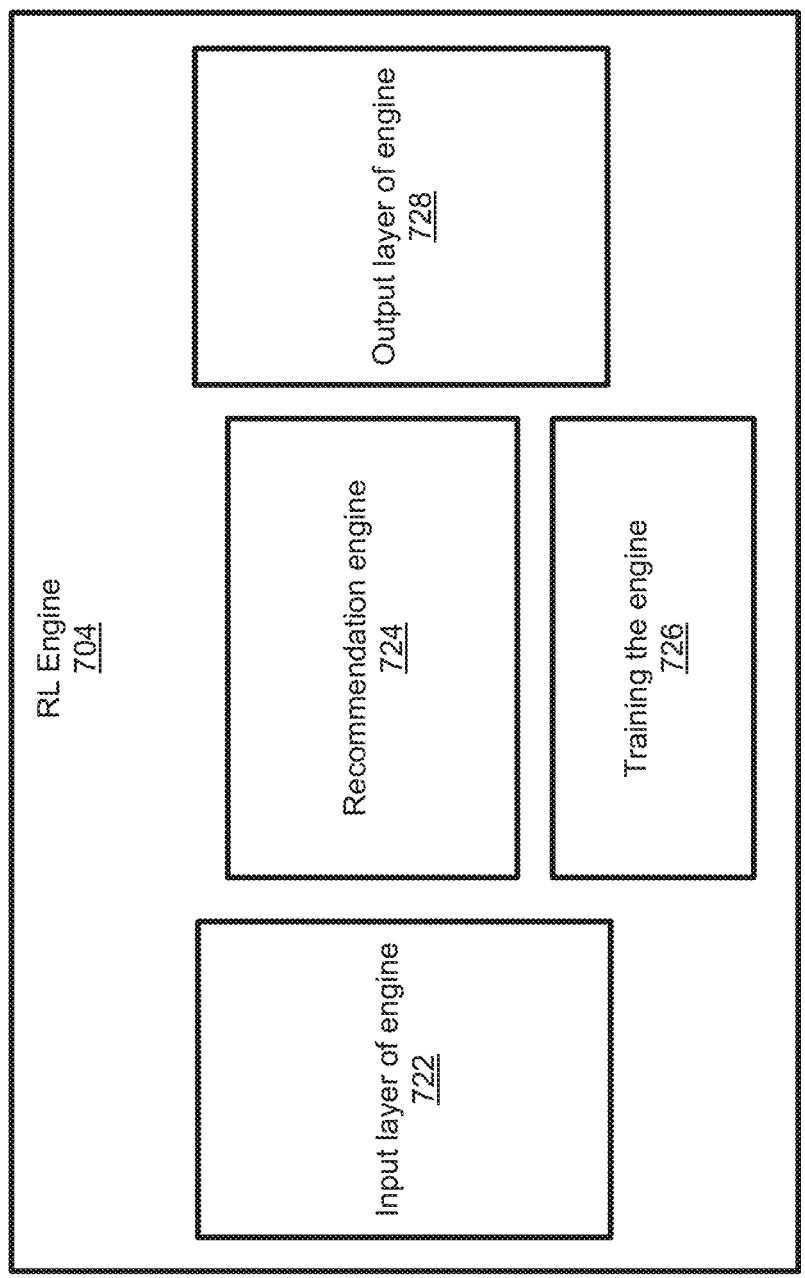
FIG. 7B illustrates an RL engine employed in the workflow, according to an embodiment.

The analytics server may first receive patient data 702 for a particular patient. The patient data 702 may include medical images and/or patient information. The patient data 702 may be ingested by reinforcement learning (RL) engine 704. FIG. 7B illustrates a RL engine 704 employed in the workflow 700, according to an embodiment.

The input layer of engine 722 is used to ingest patient data that may be heterogeneous. In some implementations, the input layer of engine 722 may reduce the dimensionality of the patient data. For example, the input layer of the engine 722 may be implemented using a convolutional layer and/or a pooling layer. The convolutional layer may receive the patient data (or a pre-processed version of the patient data). For example, pre-processing the patient data may include the analytics server normalizing the patient data, scaling the patient data, flattening the patient data, transforming the patient data into a different dimension, and the like.

An example convolutional layer in the input layer of engine 722 detects and extracts features of the patient data (e.g., patient data 702 in FIG. 7A) by convolving a filter and/or kernel with the patient data and generating a feature map of the extracted features. Convolving the patient data with the filter has the effect of reducing the dimensions of the patient data.

The output of the convolutional layer may be a feature map. In some embodiments, there may be one or more convolutional layers after the convolutional layer. Increasing the number of convolutional layers increases the complexity of the features detected in the feature map. If additional convolutional layers are employed, the filters in the subsequent convolutional layers may be the same as the filters employed in the first convolutional layer. Additionally, or alternatively, the filters used in the subsequent convolutional layers may be different from the filters employed in the first convolutional layer.

The feature map may be fed into a pooling layer. The pooling layer may be a max pooling layer (or any other type of pooling later) that detects prominent features. In other configurations, the pooling layer may be an average pooling layer. The pooling layer reduces the dimensionality of the feature map to down sample the feature map for more efficient operation. In an example, if the pooling layer is a max pooling layer, then the analytics server detects the prominent features having higher relative values in a pooling window.

The recommendation engine 724 may be a machine learning model (e.g., a neural network) or a generalized linear model based on input features determined from the input layer of engine 722. The recommendation engine 724 may be a global engine (e.g., global model 432 in FIG. 4) or include separate sub-engines for each radiotherapy attribute (and/or category of radiotherapy treatment). Accordingly, there may be n models indicating n field geometry attribute options.

The output layer of the engine 728 may convert an output from the recommendation engine 724 into a recommendation score (or other probability associated with a medical professional's predicted field geometry attribute preference). In the event the recommendation engine 724 is a neural network, for instance, the output layer of the engine 728 may be a softmax layer. The softmax layer may use a softmax function, or a normalized exponential function, to transform an input of real numbers (e.g., the output of the recommendation engine 724) into a normalized probability distribution over predicted output classes (e.g., radiotherapy treatment attributes and/or categories of radiotherapy treatment). In the event the recommendation engine 724 is a linear model, the output layer of the engine 728 may be a list of recommendations with an assigned probability.

The recommendation engine 724 may be trained at 726. In some configurations, the engine is trained at 726 every time the medical professional selects a radiotherapy treatment attribute. The selected radiotherapy treatment attribute is compared to the recommended radiotherapy treatment attributes and a reward is determined (e.g., reward determination 714). The engine may also be trained at 726 every predetermined number of times the medical professional selects a radiotherapy treatment attribute. That is, the engine is trained at 726 continually and in response to medical professional inputs.

In other configurations, the recommendation engine 724 may be trained at 726 during a training phase. For example, medical professionals may select radiotherapy treatment attributes and the selected radiotherapy treatment attribute is compared to the recommended radiotherapy treatment attribute only during the training phase. After the completion of the training phase (e.g., a threshold number of training iterations, a threshold recommendation accuracy), the recommendation engine 724 may not be trained. Accordingly, a training phase is clearly distinguished from a usage phase (e.g., when a medical professional uses the trained recommendation engine 724 to suggest radiotherapy treatment attributes).

In yet other configurations, the recommendation engine 724 may be trained at 726 when certain predetermined medical professionals are interacting with the recommendation engine 724. For example, only certain medical professionals may be authorized to train the recommendation engine 724. The authorized medical professionals may be determined based on seniority, experience, ownership of the clinic, and the like. When a medical professional who is not an authorized medical professional is interacting with the recommendation engine 724, the recommendation engine 724 may not be training (e.g., there is no reward determination 714). Although the recommendation engine 724 is not being trained, the recommendation engine 724 may still provide recommendations to the medical professionals. Similarly, although the recommendation engine 724 is not being trained, the click recorder 712 may still record the selected radiotherapy treatment attributes and save the information in storage (e.g., in server 120c and/or clinic server 140b in FIG. 1).

Referring back to FIG. 7A, the recommendation controller 706 may convert the output of the output layer of the engine (e.g., 728 in FIG. 7B) to an output that the analytics server displays (or otherwise communicates) to a medical professional. For example, the recommendation controller 706 may select the top n recommendations for display. In a different example, the recommendation controller 706 may rank the recommendations from most recommended to least recommended. The recommendation controller 706 may also remove the recommendation scores (or probability associated with the medical professional's predicted field geometry attribute preference) from the associated radiotherapy treatment attribute options being presented for display. Additionally, or alternatively, the recommendation controller 706 may generate a recommendation score associated with radiotherapy treatment attributes.

At 708, the analytics server may display the results from the recommendation controller 706 using an interactive display (e.g., the interactive display initialized at step 206 in FIG. 2). The medical professional may operate an electronic device configured to execute treatment planning software such that the results of the recommended radiotherapy treatment attributes (and specifically, the recommended field geometry attributes) are displayed to the medical professional.

At 710, the analytics server may transmit the recommendations selected by the medical professional to a downstream application. For example, a downstream application may be configured to identify a treatment plan given various radiotherapy treatment attributes. For instance, the field geometry attributes selected by the medical professional may be transmitted to a machine learning model to predict side effects from the radiotherapy treatment.

The click recorder 712 (e.g., an example of a monitoring system initialized in step 208 of FIG. 2) may recognize the selection of the medical professional. The selection of the medical professional may be used during reward determination 714. The RL engine 704 (and specifically, the agents 402 of the asynchronous advantage actor critic contextual bandit reinforcement learning model 400 in FIG. 4) is rewarded based on the results of the reward determination 714. For example, if the medical professional selects a radiotherapy treatment attribute recommended by the RL engine 704, the analytics server may adjust the reward associated with the policy and action associated with the recommendation of the radiotherapy attribute upwards. In contrast, if the medical professional selects a radiotherapy treatment attribute that was not recommended by the RL engine 704, the analytics server may decrease (or not adjust) the reward associated with the policy and action. In some implementations, the reward determination 714 may be based on the probability score (or recommendation score) associated with the recommendation.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A computer-implemented method comprising:
    iteratively training, by a processor, a machine learning model, wherein in at least one iteration, the processor:
        executes the machine learning model to ingest patient data to select a predicted radiotherapy treatment attribute from a plurality of treatment attribute options for a category of radiotherapy treatment from a plurality of categories of radiotherapy treatment corresponding to different radiation therapy treatment techniques;
        in response to displaying the plurality of treatment attribute options on an electronic device, receives a selection of at least one attribute;
        calculates a reward value for the predicted radiotherapy treatment attribute, wherein when the selection matches the predicted radiotherapy treatment attribute, the processor adjusts the reward value upwards;
        generates a subsequent predicted radiotherapy treatment attribute corresponding to a subsequent category of radiotherapy treatment, the processor selecting the subsequent category of radiotherapy treatment based on the selection of at least one radiotherapy treatment attribute received from the electronic device; and
        calculates a subsequent reward value for the subsequent predicted radiotherapy treatment attribute,
    wherein the processor trains a policy, using the reward value or the subsequent reward value, to generate a combination of predicted radiotherapy treatment attributes that generates a cumulative reward value that satisfies a threshold.

2. The computer-implemented method of claim 1, wherein the subsequent category of radiotherapy treatment corresponds to: couch rotation or collimator angle settings.

3. The computer-implemented method of claim 1, wherein the processor displays the plurality of treatment attribute options on the electronic device operated by a user, such that the machine learning model is trained based on the user's preferences.

4. The computer-implemented method of claim 1, wherein the patient data comprises at least one of a patient's anatomical attribute, a body mass index, a medical image, a patient height, a patient weight, a patient age, diagnosis information, or a patient equipment.

5. The computer-implemented method of claim 1, wherein the subsequent category is selected using a workflow for radiotherapy treatment.

6. The computer-implemented method of claim 1, wherein each category of radiotherapy treatment corresponds to a category of a field geometry.

7. The computer-implemented method of claim 1, further comprising:
    executing, by the processor, the trained machine learning model using data associated with a second patient; and
    displaying, by the processor, a second predicted radiotherapy treatment attribute that is predicted to produce a higher reward than other treatment attribute options.

8. The computer-implemented method of claim 1, wherein the cumulative reward value satisfying the threshold indicates that the cumulative reward value is higher than other cumulative reward values associated with other possible predicted radiotherapy treatment attributes.

9. The computer-implemented method of claim 1, wherein at least one radiotherapy treatment attribute corresponds to: a standard VMAT with two full arcs, a complex VMAT with two partial arcs, a complex VMAT with three arcs, a complex VMAT with four arcs, rotate couch, do not rotate couch, rotate couch a predetermined number of degrees, a default value collimator angle, a non-default value collimator angle, a collimator angle arc start, or a collimator angle arc stop.

10. The computer-implemented method of claim 1, wherein the machine learning model is trained using one-step reinforcement learning.

11. A system comprising:
    a server comprising a processor and a non-transitory computer-readable medium containing instructions that when executed by the processor causes the processor to perform operations comprising:
    iteratively train a machine learning model, wherein in at least one iteration, the processor:
        executes the machine learning model to ingest patient data to select a predicted radiotherapy treatment attribute from a plurality of treatment attribute options for a category of radiotherapy treatment from a plurality of categories of radiotherapy treatment corresponding to different radiation therapy treatment techniques;
        in response to displaying the plurality of treatment attribute options on an electronic device, receives a selection of at least one attribute;
        calculates a reward value for the predicted radiotherapy treatment attribute, wherein when the selection matches the predicted radiotherapy treatment attribute, the processor adjusts the reward value upwards;

generates a subsequent predicted radiotherapy treatment attribute corresponding to a subsequent category of radiotherapy treatment, the processor selecting the subsequent category of radiotherapy treatment based on the selection of at least one radiotherapy treatment attribute received from the electronic device; and calculates a subsequent reward value for the subsequent predicted radiotherapy treatment attribute, wherein the processor trains, using the reward value or the subsequent reward value, a policy to generate a combination of predicted radiotherapy treatment attributes that generates a cumulative reward value that satisfies a threshold.

12. The system according to claim 11, wherein the subsequent category of radiotherapy treatment corresponds to: couch rotation or collimator angle settings.

13. The system according to claim 11, wherein the processor is further configured to display the plurality of treatment attribute options on the electronic device operated by a user such that the machine learning model is trained based on the user's preferences.

14. The system according to claim 11, wherein the patient data comprises at least one of a patient's anatomical attribute, a body mass index, a medical image, a patient height, a patient weight, a patient age, diagnosis information, or a patient equipment.

15. The system according to claim 11, wherein the subsequent category is selected using a workflow for radiotherapy treatment.

16. The system according to claim 11, wherein each category of radiotherapy treatment corresponds to a category of a field geometry.

17. The system according to claim 11, wherein the processor is further configured to:

execute the trained machine learning model using data associated with a second patient; and display a second predicted radiotherapy treatment attribute that is predicted to produce a higher reward than other treatment attribute options.

18. The system according to claim 11, wherein the cumulative reward value satisfying the threshold indicates that the cumulative reward value is higher than other cumulative reward values associated with other possible predicted radiotherapy treatment attributes.

19. The system according to claim 11, wherein at least one radiotherapy treatment attribute corresponds to: a standard VMAT with two full arcs, a complex VMAT with two partial arcs, a complex VMAT with three arcs, a complex VMAT with four arcs, rotate couch, do not rotate couch, rotate couch a predetermined number of degrees, a default value collimator angle, a non-default value collimator angle, a collimator angle arc start, or a collimator angle arc stop.

20. The system according to claim 11, wherein the machine learning model is trained using one-step reinforcement learning.

* * * * *